United States Patent
Lai

(10) Patent No.: US 6,201,849 B1
(45) Date of Patent: Mar. 13, 2001

(54) APPARATUS AND METHOD FOR RECONSTRUCTION OF VOLUMETRIC IMAGES IN A HELICAL SCANNING CONE-BEAM COMPUTED TOMOGRAPHY SYSTEM

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/374,679

(22) Filed: Aug. 16, 1999

(51) Int. Cl.⁷ .......................................................... A61B 6/03
(52) U.S. Cl. .................................. 378/4; 378/15; 378/901
(58) Field of Search ................................. 378/4, 8, 15, 17, 378/901

(56) References Cited

U.S. PATENT DOCUMENTS

| 5,802,134 | 9/1998 | Larson et al. ............................... 378/4 |
| 5,909,477 | * 6/1999 | Crawford et al. ......................... 378/4 |

OTHER PUBLICATIONS

Feldkamp, L.A., et al., "Practical ConeBeam Algorithm", J. Opt. Soc. Am. vol. 1, No. 6, Jun. 1984, pp. 612–619.

Yan, X., et al., "Cone–Beam Tomography with Circular, Elliptical and Spiral Orbits", Phys. Med. Biol. vol. 37, No. 3, Nov. 1991, pp. 493–506.

Schaller, S., et al., "New Efficient Fourier–Reconstruction Method For Approximate Image Reconstruction In Spiral Cone–Beam CT At Small Cone Angles", SPIE, vol. 3032, Feb. 1997, pp. 213–225.

Wang, G., et al., "A General Cone Beam Algorithm", IEEE, vol. 12, Sep. 1993, pp. 486–496.

Kudo, H., et al., "Helical–Scan Computed Tomography Using Cone–Beam Projections", Journal of Electronics, Information, and Communication Society, J74–D–II, 1991, pp. 1108–1114.

* cited by examiner

Primary Examiner—David V. Bruce
(74) Attorney, Agent, or Firm—McDermott, Will & Emery

(57) ABSTRACT

An apparatus and method for reconstructing image data for a region are described. A radiation source and an array of detectors located on opposed sides of a region are used to generate scan data for the region from a plurality of diverging radiation beams, i.e., a cone beam. The cone beam scan data for the region are converted into parallel beam scan data. The reordered parallel beam scan data are used to generate projection data related to a set of oblique slices for the region, wherein the oblique slices form a non-perpendicular angle with the longitudinal axis of the region. Convolution is applied to the projection data related to each oblique slice. The image data for the region are then generated by three-dimensional back projection of the convoluted projection data along the paths of the interpolated rays.

27 Claims, 9 Drawing Sheets

APPARATUS AND METHOD FOR RECONSTRUCTION OF VOLUMETRIC IMAGES IN A HELICAL SCANNING CONE-BEAM COMPUTED TOMOGRAPHY SYSTEM

FIELD OF THE INVENTION

The present invention relates generally to computed tomography (CT) imaging and more particularly to three-dimensional CT imaging of helical cone beam scanning with improved efficiency and reduced image artifacts.

BACKGROUND OF THE INVENTION

FIG. 1 is a schematic axial view of a conventional third generation CT scanner 10 which includes an x-ray source 12 and an x-ray detector system 14 secured to diametrically opposite sides of an annular shaped disk 16. The disk 16 is rotatably mounted within a gantry support (not shown), so that during a scan the disk 16 continuously rotates about a longitudinal z-axis while x-rays pass from the source 12 through an object, such as a patient 20, positioned on a patient table 56 within the opening of the disk 16. The z-axis is normal to the plane of the page in FIG. 1 and intersects the scanning plane at the mechanical center of rotation 18 of the disk 16. The mechanical center of rotation 18 of the disk corresponds to the "isocenter" of the reconstructed image.

In one conventional system, the detector system 14 includes an array of individual detectors 22 disposed in a single row in a shape of an arc having a center of curvature at the point 24, referred to as the "focal spot," where the radiation emanates from the x-ray source 12. The source 12 and array of detectors 22 are positioned so that the x-ray paths between the source and each detector all lie in a "scanning plane" that is normal to the z-axis. Since the x-ray paths originate from what is substantially a point source and extend at different angles to the detectors, the diverging x-ray paths form a "fan beam" 26 that is incident on the detector array 14 in the form of one-dimensional linear projection. The x-rays incident on a single detector at a measuring instant during scan are commonly referred to as a "ray," and each detector generates an output signal indicative of the intensity of its corresponding ray. The angle of a ray in space depends on the rotation angle of the disk and the location of the detector in the detector array. Since each ray is partially attenuated by all the mass in its path, the output signal generated by each detector is representative of the attenuation of all the mass disposed between that detector and the x-ray source, i.e., the attenuation of the mass lying in the detector's corresponding ray path. The x-ray intensity measured by each detector is converted by a logarithm function to represent a line integral of the object's density, i.e., the projection value of the object along the x-ray path.

The output signals generated by the x-ray detectors are normally processed by a signal processing portion (not shown) of the CT system. The signal processing portion generally includes a data acquisition system (DAS) which filters the output signals generated by the x-ray detectors to improve their signal-to-noise ratio (SNR). The output signals generated by the DAS during a measuring interval are commonly referred to as a "projection", "projection profile", or "view" and the angular orientation of the disk 16, source 12 and detector system 14 corresponding to a particular projection profile is referred to as the "projection angle."

If the detector array consists of N detectors, then N projection values are collected for each rotation angle. With the rays in a fan shape, these N projection values are collectively called a fan-beam projection profile of the object. The data of fan-beam projection profiles are often reordered or rebinned to become parallel-beam projection profiles. All rays in a parallel-beam profile have the same angle, called the parallel-beam projection view angle $\phi$. The image of the object can be reconstructed from parallel-beam projection profiles over a view angle range of 180°.

During a scan, the disk 16 rotates smoothly and continuously around the object being scanned, allowing the scanner 10 to generate a set of projections at a corresponding set of projection angles. In a conventional scan, the patient remains at the constant z-axis position during the scan. When obtaining multiple scans, the patient is stepped along the longitudinal z-axis between scans. These processes are commonly referred to as "step-and-shoot" scanning or "constant-z-axis" (CZA) scanning. Using well-known algorithms, such as the inverse Radon transform, a tomogram may be generated from a set of projections that all share the same scanning plane normal to the z-axis. This common scanning plane is typically referred to as the "slice plane."

A tomogram is a representation of the density of a two-dimensional slice along the slice plane of the object being scanned. The process of generating a tomogram from the projections is commonly referred to as "reconstruction," since the tomogram may be thought of as being reconstructed from the projection data. The reconstruction process can include several steps including reordering to form parallel-beam data from the fan-beam data, convolution to deblur the data, and back projection in which image data for each image pixel is generated from the projection data. In CZA scanning, for a particular image slice, all the projections share a common scanning plane, so these projections may be applied directly for convolution and to the back projector for generation of a tomogram.

The step-and-shoot CZA scanning approach can be a slow process. During this time consuming approach, the patient can be exposed to high amounts of x-ray radiation. Also, as the scanning table is moved between each scan, patient motion can result, causing motion and misregistration artifacts which result in reduced image quality.

Several approaches have been developed to decrease the time required to obtain a full scan of an object. One of these approaches is helical or spiral scanning in which the object being scanned is translated along the z-axis while the disk 16 with source 12 and linear detector array 14 are rotated about the patient. In helical scanning, the projections are normally acquired such that the position z is linearly related to the view angle. This form of helical scanning is commonly referred to as constant-speed-helical (CSH) scanning.

FIG. 2A illustrates the data collected during a conventional CZA scan, and FIG. 2B illustrates the data collected during a CSH scan. As shown in FIG. 2A, if the x-ray source 12 and the detector system 14 are rotated about the object 20 while the object remains at a fixed z-axis location, the scanning planes associated with all the projections collected by the detector system 14 will all lie in a common slice plane 50. As shown in FIG. 2B, if the object 20 is continuously translated in the direction of the z-axis while the disk is rotated about the object 20, none of the scanning planes will be coplanar. Rather, the scanning plane associated with each projection will lie at a unique position along the z-axis at a locus point on a helical set of loci. FIG. 2B illustrates the z-axis coordinate of the scanning planes corresponding to helical projection angles in the interval $(0, 10\pi)$.

In CZA scanning, all the projections share a common scanning plane, so these projections may be applied to the back projector after convolution to generate a tomogram. In CSH scanning however, each projection has a unique scanning plane located at a unique z-axis coordinate, so CSH projections may not be applied to a back projector. However, the data collected during a CSH scan can be interpolated in various fashions to generate a set of interpolated projections that do all share a common scanning plane extending normal to the z-axis. Each interpolated projection, for example, may be generated by combining two projections taken at equivalent projection angles and at different z-axis positions. These interpolated projections may be treated as CZA data and applied after convolution to a back projector to generate a tomogram.

CSH scanning requires some form of interpolation to generate a tomogram, and tomograms generated by CSH scanning therefore tend to be characterized by image artifacts. Also, since the CSH scan projection data, which are collected over an interval of z-axis locations, are combined to generate the interpolated CZA scan data, tomograms generated during CSH scanning have a wider effective slice plane width and, therefore, lower z-axis resolution, than tomograms generated by CZA scanning. However, helical scanning advantageously permits rapid scanning of a large volume of a patient. For example, in a time interval short enough to permit a patient comfortably to hold his or her breath (and thereby remain relatively motionless), a helical scan can collect enough data to fully scan an entire organ such as a kidney.

Another approach to decreasing scan time over CZA scanning is commonly referred to as "cone-beam scanning," in which a three-dimensional volume of the object or patient is scanned at once. In cone-beam scanning, the detection system includes a two-dimensional array of detectors instead of the one-dimensional array used in conventional scanning. The x-ray output from the source diverges in two dimensions to produce the equivalent of multiple fan beams, referred to as a "cone beam," along the z-axis dimension which illuminate multiple rows of plural detectors and therefore form a two-dimensional projection on the array.

In one form of a cone-beam system, the patient or object is maintained in a stationary z-axis position while the source and two-dimensional detector array are rotated around the patient or object. The patient is then moved to a new z-axis position, and the scan is repeated. In this type of step-and-shoot or "stationary cone beam" system, rather than sweeping out a plane, a volume of the object is scanned. After one volume is scanned, the source and detector are stepped along the z-axis to scan the next volume. Still another approach used to decrease scan time is helical cone-beam (HCB) scanning, in which a cone-beam configuration, i.e., a source and two-dimensional detector array, are rotated around the patient while the patient is continuously translated in the z-direction.

One approach to reconstructing volumetric image data is to divide it into a stack of slices. Standard two-dimensional reconstruction techniques, such as 2D filtered back projection (FBP), are used to reconstruct CZA and interpolated CSH data in non-cone-beam systems. FBP requires that the set of projections used for reconstruction of slices lie in the same plane. This condition is satisfied in CZA scanning, and interpolation is used in CSH scanning to produce a set of interpolated or simulated linear projections which effectively meet this requirement. In either case, 2D FBP is an efficient means of producing image data from the 1D fan beam projection data.

In cone-beam geometry, the required condition is only satisfied for a detector row coplanar with the source in a plane perpendicular to the z-axis, usually the center detector row. An image data slice perpendicular to the z-axis will be referred to herein as a normal slice. Other slices, i.e., slices which form a non-perpendicular angle with the z-axis, are referred to herein as oblique slices or tilted slices. In cone-beam CT, a 1D projection defined by the source and a given detector row will intersect a different slice in the object as the gantry rotates. For a helical cone beam scan, no slice is coplanar with the rays in all view angles. Conventional 2D FBP can be used to reconstruct cone-beam data by treating each row as an independent 1D projection. This approximation ignores the cone-beam geometry and results in image artifacts such as streaks and lowering of the reconstructed density.

The approximation can be improved by selecting certain oblique slices for the 2D reconstruction. One such approach is described in U.S. Pat. No. 5,802,134 (the '134 patent), entitled "Nutating Slice CT Image Reconstruction Apparatus and Method," and assigned to the same assignee as the present application. The contents of that patent are incorporated herein in their entirety by reference. In the approach described in the '134 patent, a 2D fan-beam projection profile can be interpolated from the cone-beam data for each slice at each rotation angle. The slice can be reconstructed from the fan-beam projection profiles over a sufficient number of rotation angles. In this prior method, the projection profiles are interpolated directly from the actual cone-beam data. The mathematical relation between the interpolated rays of a projection profile and the original rays are complex. Because of this complexity, the prior method included a procedure based on computer simulation of scanning the oblique slice to determine the locations of interpolating rays. The result of the simulation depends on the accuracy of simulation.

An approximate method used to reconstruct stationary cone-beam data is known as the Feldkamp algorithm and is described in L. A. Feldkamp, et al.,"Practical cone-beam algorithm," *J. Opt. Soc. Am.* 1, pp. 612–619, (1984).

In the Feldkamp algorithm, the rays are back projected in the three-dimensional cone. Algorithms such as Feldkamp, which attempt to incorporate the true cone-beam geometry of the data, are referred to as three-dimensional filtered back projection (3D-FBP) algorithms. Three-dimensional algorithms reconstructing HCB data have also been developed. Examples of these algorithms are described in the following papers.

1. H. Kudo and T. Saito, "Three-dimensional helical-scan computed tomography using cone-beam projections," *Journal of Electronics, Information, and Communication Society*, J74-D-II, 1108–1114, (1991).

2. D. X. Yan and R. Leahy, "Cone-beam tomography with circular, elliptical and spiral orbits," *Phys. Med. Biol.* 37, 493–506, (1992).

3. S. Schaller, T. Flohr and P. Steffen,"New efficient Fourier reconstruction method for approximate image reconstruction in spiral cone-beam, CT at small cone angles," *SPIE International Symposium on Medical Imaging*, February, 1997.

4. G. Wang, T-H Lin, P. Cheng and D. M. Shinozaki, "a general cone beam algorithm," *IEEE Trans. Med. Imag.* 12, 486–496, (1993).

A cone-beam reconstruction method using 3D back-projection for cone-beam helical scans is described in copending U.S. patent application Ser. No. 09/038,320, entitled, "Method and Apparatus for Reconstructing Volumetric Images in a Helical Scanning Computed Tomography System with Multiple Rows of Detectors," by C. M. Lai, filed on Mar. 11, 1998, of common assignee. In the approach described therein, at each view angle, the projection profile is interpolated from the collected cone-beam data for a slice normal to the z-axis. Such interpolated projection profiles are then convoluted with a well known kernel as in a 2D image reconstruction for all view angles. The convoluted projection profiles from a number of slices at successive z positions are then backprojected to a 3D matrix to reconstruct the volumetric image of the object. In this 3D backprojection, the convoluted projection values are backprojected to the voxels along the rays for which they were measured, and each voxel is backprojected from one convoluted projection value at each view angle. In this cone-beam reconstruction method, the backprojection is computed accurately, but the convolution operation is an approximation.

If the projection profiles were simply backprojected from all view angles without the convolution operation, the spatial resolution image would be highly reduced as if the image were filtered by a very low-pass filter. The purpose of convolution is to compensate for such a low-pass filtering effect. An exact convolution kernel can be derived for such compensation, and an accurate image can be reconstructed by convoluting the projection profile with this kernel. However, it requires that all rays of the projection profiles lie on the same plane in all view angles. Deviation from this coplanar condition will introduce errors into the convoluted projection data. In the conventional CT scanner with a single row of detectors, all projections are either measured from the same slice or interpolated from two parallel slices to the same slice for convolution. Therefore, accurate images can be reconstructed.

In a cone-beam system, the projection profiles measured from different view angles are not on the same plane because of the cone angle. For a step-and-shoot scan, the projection profiles measured by the central row of detectors do stay on the same plane in all view angles. Thus the central slice can be reconstructed accurately. However, other slices will contain error as the result of deviation from the coplanar condition. In a helical scan, the condition is worse. At each view angle, the projection profile has to be interpolated from the projection values measured by different rows of detectors to a selected slice for convolution. Therefore, even for the central slice, the interpolated projection profiles do not satisfy the coplanar condition for all view angles.

SUMMARY OF THE INVENTION

The present invention is directed to a method and apparatus for reconstructing image data for a region having a longitudinal axis. A radiation source and an array of detectors are located on opposed sides of the region. The radiation source emits radiation toward the array of detectors to generate a plurality of diverging radiation beams received by the array of detectors. At least one of the radiation source and the array of detectors is rotatable about the longitudinal axis through a plurality of projection angles to scan the region to generate diverging beam scan data for the region. The diverging beam scan data for the region is converted into parallel beam scan data. At least one data slice for the region is defined such that the data slice is oblique with respect to the longitudinal axis. At least a portion of the parallel beam scan data for the region is used to generate projection data associated with the at least one oblique data slice. Convolution is applied to the projection data associated with the oblique slice to generate convoluted projection data for the region. A three-dimensional back projection is then applied to the convoluted projection data associated with the at least one oblique slice to generate the image data for the region.

In one embodiment, the array of detectors is a two-dimensional array of detectors. In this embodiment, the plurality of diverging radiation beams form a cone-beam of radiation. In this embodiment, the invention is applicable to diverging beam scan data acquired by helical cone-beam scanning.

An angle formed by the oblique slice and the longitudinal axis is selected such that the slice is coplanar with the radiation source for at least one projection angle. In particular, in one embodiment, the angle of the oblique slice is selected such that the slice is coplanar with the radiation source for three projection angles. Specifically, the slice can be selected such that it is coplanar with the radiation source at projection angles of 0°, 90° and 180°.

In one embodiment, the projection data associated with the at least one oblique slice is generated using parallel beam scan data for a ray that intersects the at least one oblique slice. In one particular embodiment, the ray intersects the middle of the oblique slice. Alternatively, the projection data associated with the at least one oblique slice is generated using the diverging beam scan data for a ray intersecting the oblique slice.

The approach of the invention to 3D image reconstruction provides advantages over prior approaches. The use of an oblique slice as opposed to a normal slice reduces errors and, therefore, substantially reduces artifacts in the produced image. The angle of the oblique slice selected in one embodiment of the invention allows the slice to be coplanar with the radiation source from multiple projection angles, resulting in reduced image artifacts. Also, because the data for the oblique slice is generated using parallel-beam scan data, computational complexity of the approach is substantially less than that of prior systems.

In the approach described herein, a better approximation is developed to improve the convolution operation. It generates more accurate convoluted projection profiles for 3D backprojection, and thus reconstructs more accurate volumetric images than the prior art.

In the present invention, oblique slices, rather than normal slices, are selected for convolution. The projection data can be interpolated to any slice for convolution. As long as all the interpolated rays are known, 3D backprojection can be performed from the interpolated and convoluted projection data. In order for a slice to be coplanar with the rays in all view angles, the focal spot must lie on the plane of that slice at all view angles. Unfortunately, no slice can meet that requirement under constant speed translation of a helical scan. Thus, instead of looking for a perfect coplanar slice, the technique of the present invention is to find a slice as coplanar with the rays as possible. Projection profiles are then interpolated from the collected data to be as close to that slice as possible for convolution and backprojection.

Certain oblique slices are more coplanar with the rays than the normal slices. The present approach selects a set of oblique slices at successive z locations for interpolating the projection data. If the interpolated projection profiles were perfectly coplanar with these slices, the images would be reconstructed as accurate as a system with zero cone angle. Since these slices do not meet the perfect coplanar condition, the reconstruction of these images is still an approximation. However, it is a good approximation, better than the prior art of selecting normal slices for convolution.

Because the projection values are interpolated to the selected slices with oblique angles, the interpolated rays are not at constant z-positions within the same slice. Furthermore, the selected oblique slices are not parallel to each other. The rays interpolated to these oblique slices do not have equal spacing in the z dimension. Although it is possible to perform 3D backprojection based on these projection profiles, the amount of computation is considerably greater than the prior method based on interpolated projection profiles of normal slices. In accordance with one aspect of the invention, a pre-interpolation technique is applied to deal with this complexity. In accordance with this pre-interpolation technique of the invention, the spacing of the convoluted projection data in the z dimension is made equal for the 3D back projection.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS OF THE INVENTION

In the present invention, cone-beam projection data are first reordered or rebinned into parallel-beam data. The data collected by each row of detectors are reordered into parallel-beam projections. A stack of oblique slices at successive z locations is selected as the references for interpolating projection profiles from the reordered projection data. Each slice is selected to be as coplanar with the rays as possible. At each view angle, a projection profile is interpolated from the reordered projection data at the rays most coplanar with the oblique slice. The projection profiles interpolated to the same oblique slice at different view angles are treated like the projection profiles of a single-row detector system for convolution. At each view angle, the stack of convoluted projection profiles, each interpolated to an oblique slice, are then used together for 3D backprojection. The convoluted data are back-projected to a 3D image matrix along the paths of the interpolated rays.

In order for a reference slice to be coplanar with the rays in all view angles, the focal spot or source must lie on the plane of that slice at all view angles. However, no slice can meet that requirement in a helical scan with constant translation speed. Thus, a slice most coplanar with the rays is selected as a reference slice to interpolate the projection data for convolution and 3D back projection. Projection profiles are interpolated from the collected data to best represent that slice.

Figure 1:
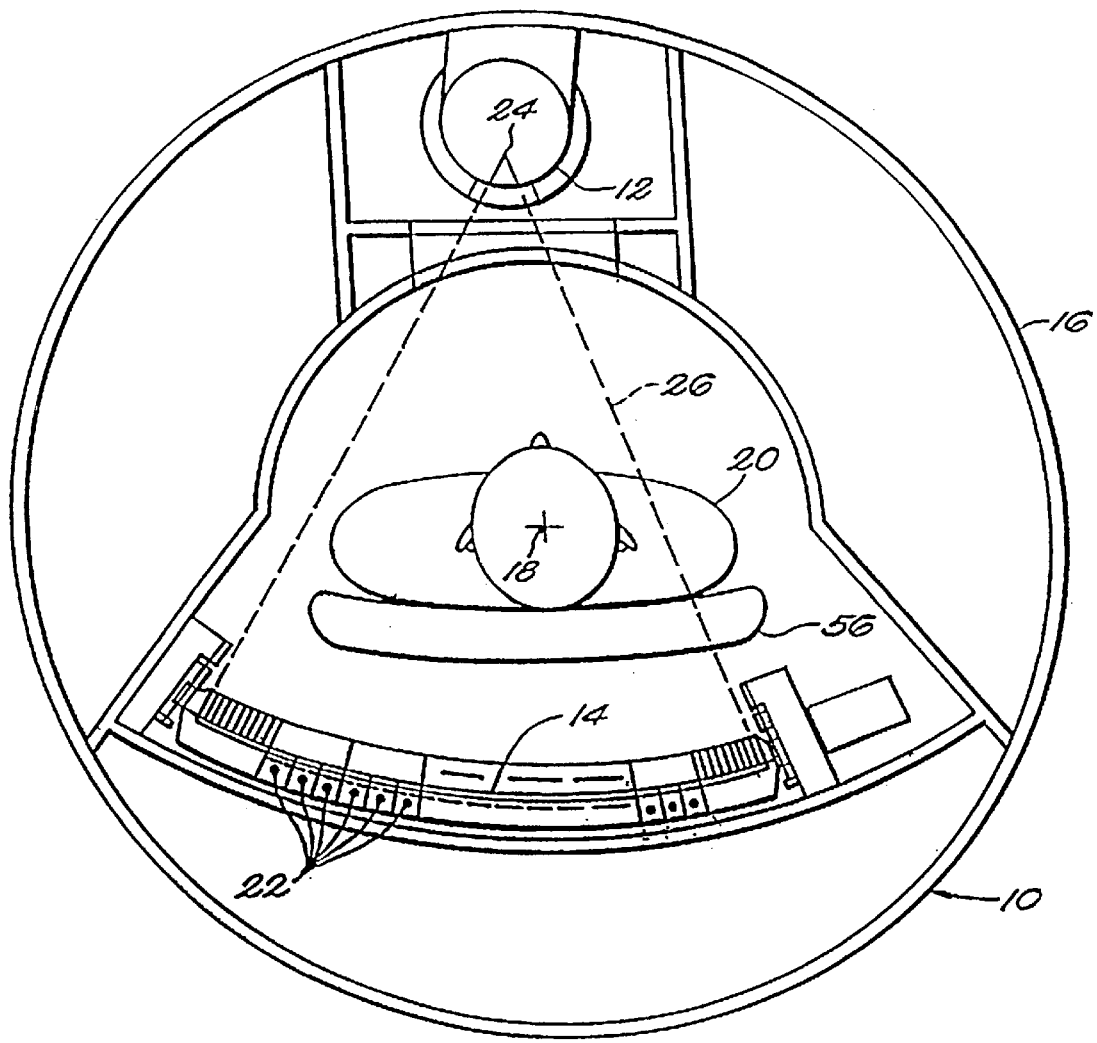
FIG. 1 is a schematic axial view of a typical computed tomography (CT) scanning system.
Figure 2A:
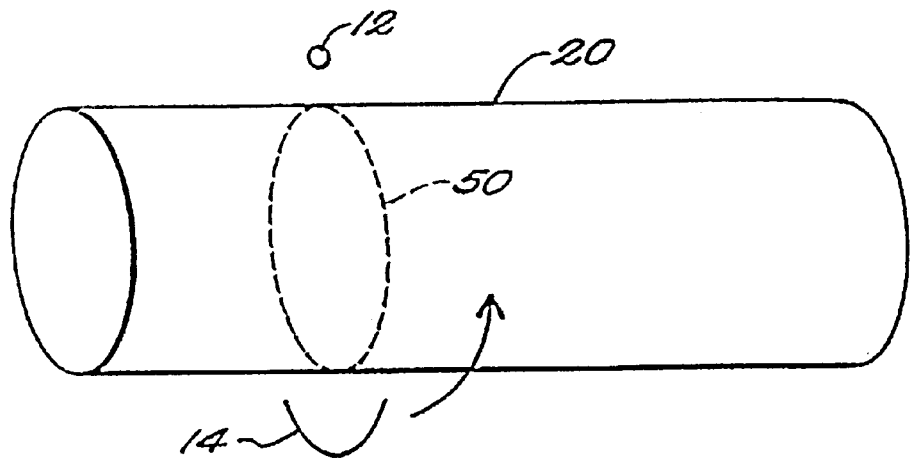
FIG. 2A illustrates the scanning path for a constant z-axis (CZA) scanning mode in a CT scanning system.
Figure 2B:
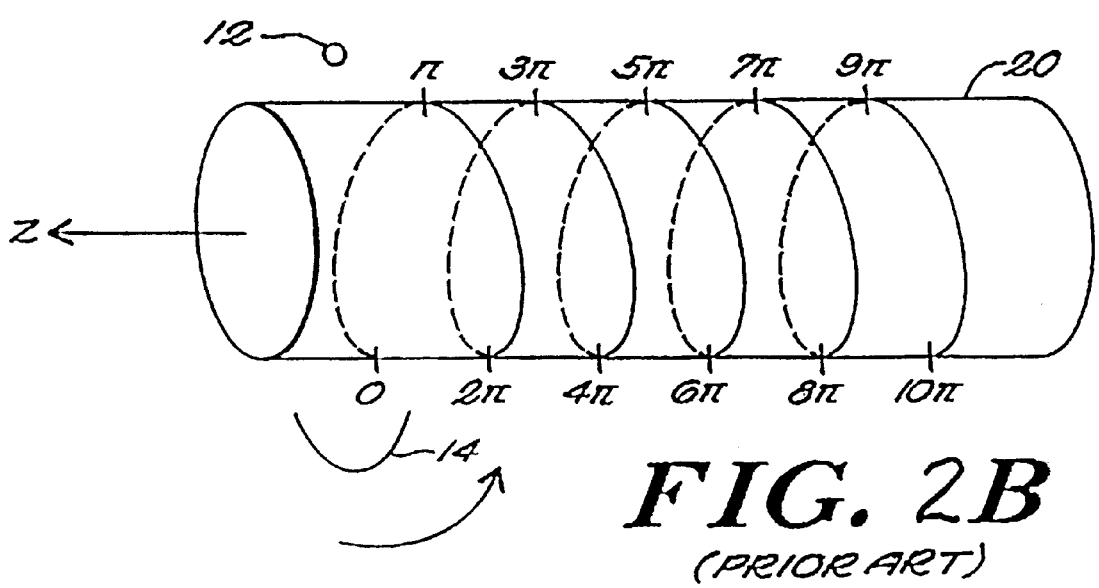
FIG. 2B illustrates the scanning path for constant-speed-helical (CSH) scanning in a CT scanning system.
Figure 3:
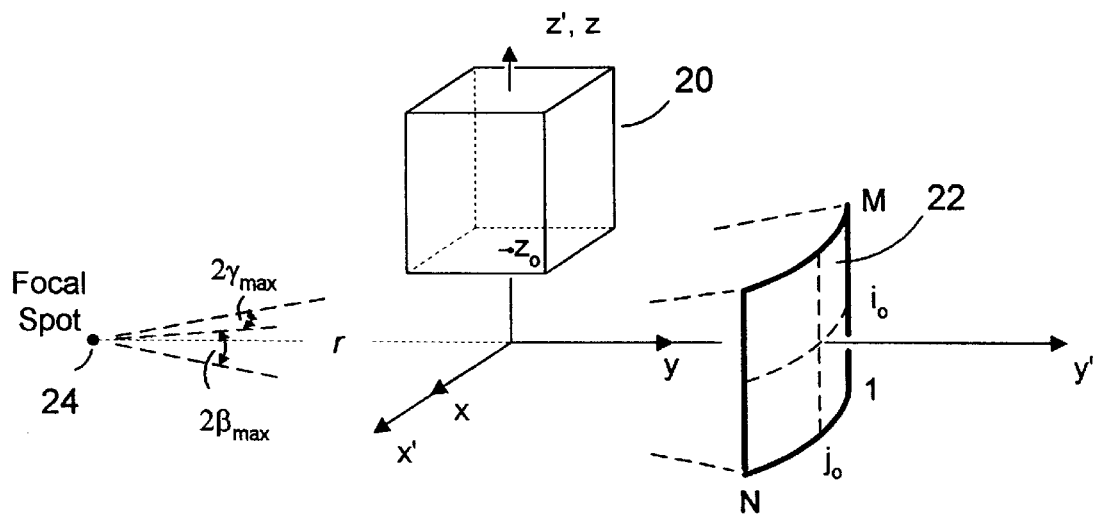
FIG. 3 is a schematic diagram which illustrates a scan object, the focal spot and detector array in a CT scanning system in accordance with the invention.
Figure 4:
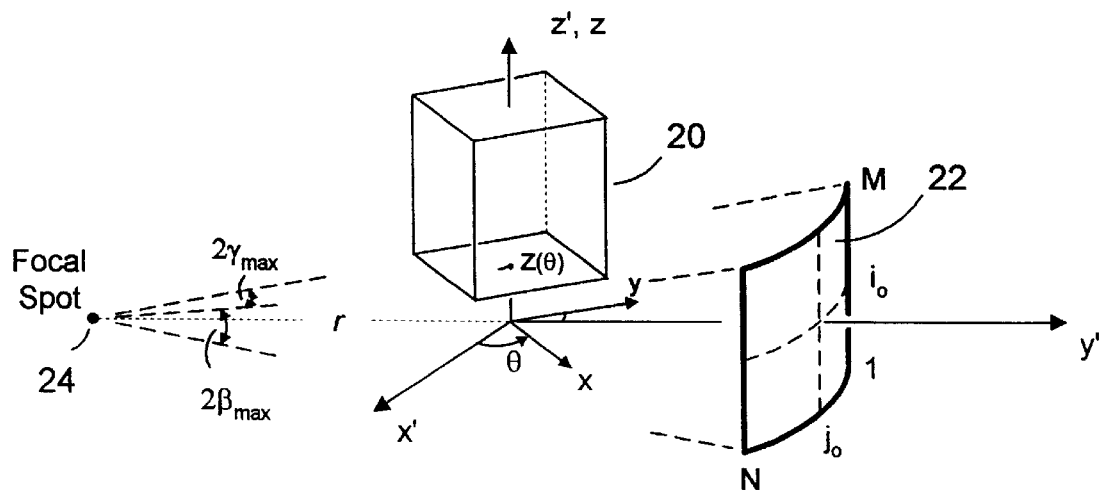
FIG. 4 is a schematic diagram which illustrates the system of FIG. 3 with 45 degrees of rotation.

FIG. 3 contains a schematic diagram illustrating a location and orientation of a scanned object 20 with respect to the focal spot 24 and the detector array 22 in a rotating frame at a starting rotation angle of θ=0, including a 3D matrix representing the image intensity of the scanned object 20. The focal spot 24 and the detector array 22 are fixed in a rotating frame of reference x'y'z', while the 3D matrix is referenced to a laboratory frame of reference xyz with the first slice located at $z=z_0$. Assuming the rotating frame is rotating clockwise about the z axis during a scan, the 3D matrix is then rotating counterclockwise about the z axis with respect to the rotating frame. During a helical scan, the 3D matrix is also traveling at a constant speed in the −z direction with respect to the laboratory frame. The geometry of the 3D matrix at rotation angle of θ=45°, for instance, is depicted in FIG. 4 as viewed in the rotating frame. The pitch of a helical scan is defined as the translation distance of the object along the z axis during a 360° rotation. If the pitch is 2p, the first slice of the 3D matrix is then located at $$z(\theta) = z_o - p\theta/\pi \quad (1)$$

The detector array 22 includes M rows of detectors. For each row, there are N detectors, or channels. Detectors from the same channel of different rows constitute a column. Thus, the detector array can also be described as N columns of detectors. Usually, N is much greater than M. The N rays measured by each row of detectors will be referred to herein as a transverse fan, since they are radiated from the focal spot 24 and lie on a plane substantially transverse to the z-axis. The M rays measured by each column of detectors will be referred to as a "longitudinal" fan, since they are also radiated from the focal spot 24 but lie on a plane parallel to the z-axis. In the typical system of the present invention, the fan angle of a transverse fan is $2\gamma_{max}$, preferably in the order of about 60° as in a convention single-row detector system, while the fan angle of a longitudinal fan is the cone angle $2\beta_{max}$, which preferably is in the order of a few degrees. The cone beam system can be considered as having M transverse fans in a large fan angle or N longitudinal fans in a small fan angle.

Figure 5:
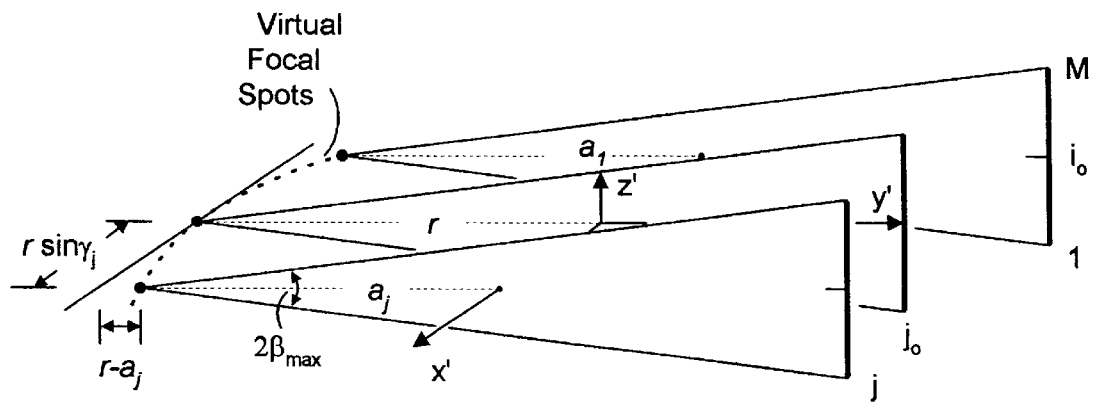
FIG. 5 is a schematic diagram which illustrates reordered rays consisting of N longitudinal fans in parallel, in accordance with the invention.

At each rotation angle, the data of a transverse fan comprises a fan-beam projection profile, as in a conventional single-row detector system. Each projection value in the projection profile is measured along the ray at an angle $\gamma_j$ relative to the ray of the channel on the y axis (the central channel if one assumes a symmetric array). It is preferable to reorder each fan-beam projection profile into a parallel-beam projection profile, as in parallel-beam reconstruction of 2D image for single-row detector system. The reordering is performed on each row independent of the data in other rows. The reordered rays consist of N longitudinal fans in parallel, as shown in FIG. 5 for a step-and-shoot scan. In FIG. 5, the focal spot of the central longitudinal fan is located at y'=−r, while the focal spot of a typical fan j>$j_o$ is located at y'=−$a_j$, with $a_j$<r. Each longitudinal fan is a virtual fan mapped from a longitudinal fan in the actual cone-beam configuration. Thus, reordered rays contain N virtual focal spots and have a contour of a wedge shape.

Figure 6:
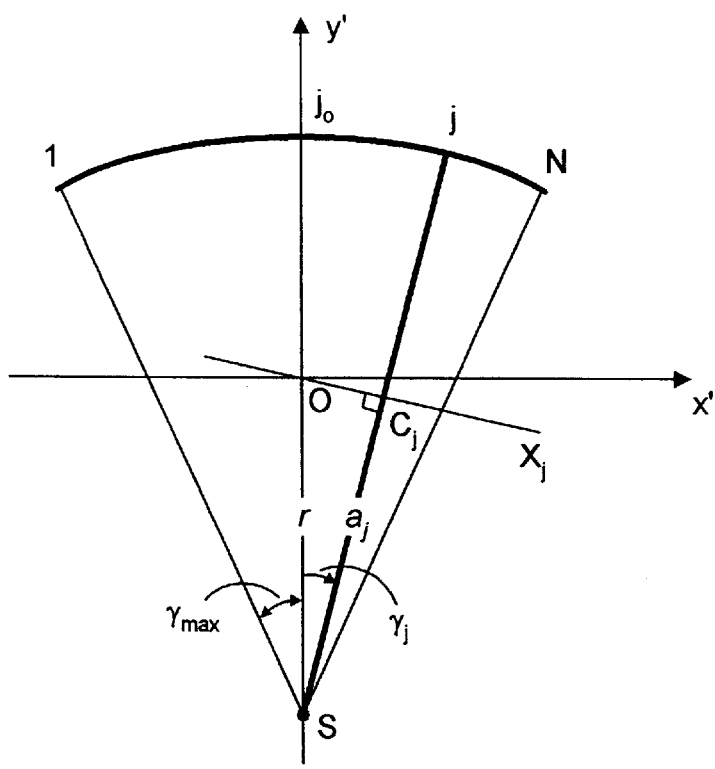
FIG. 6 is a detailed schematic illustration of a central transverse fan of FIG. 5, in accordance with the invention.

The exact location of a virtual longitudinal fan j with respect to the central longitudinal fan $j_o$ can be seen from the central transverse fan shown in FIG. 6, where each ray is the central ray of a longitudinal fan. In FIG. 6, the line $OX_j$ is normal to the longitudinal fan j with $C_j$ being the intersecting point, and it is mapped into the x'-axis of the reordered geometry in FIG. 5. The distance $a_j$ is the distance between the focal spot S and the point $C_j$, with $$a_j = r \cos \gamma_j = r \cos(j-j_o) \delta) \qquad (2)$$

where $\delta$ is the angular spacing between adjacent detector channels which gives the angle $\gamma_j=(j-j_o)\delta$. The distance $OC_j$ is the distance between a longitudinal fan j and the central longitudinal fan $j_o$. It is equal to r sin $\gamma_j$, or r sin$(j-j_o)\delta$). Because the distance $a_j$ depends on j, the virtual focal spots in the reordered geometry do not lie on a straight line. Also, the virtual longitudinal fans are not located at equal intervals along the x'-axis, as the result of nonlinear dependence of $OC_j$ on j.

Figure 7:
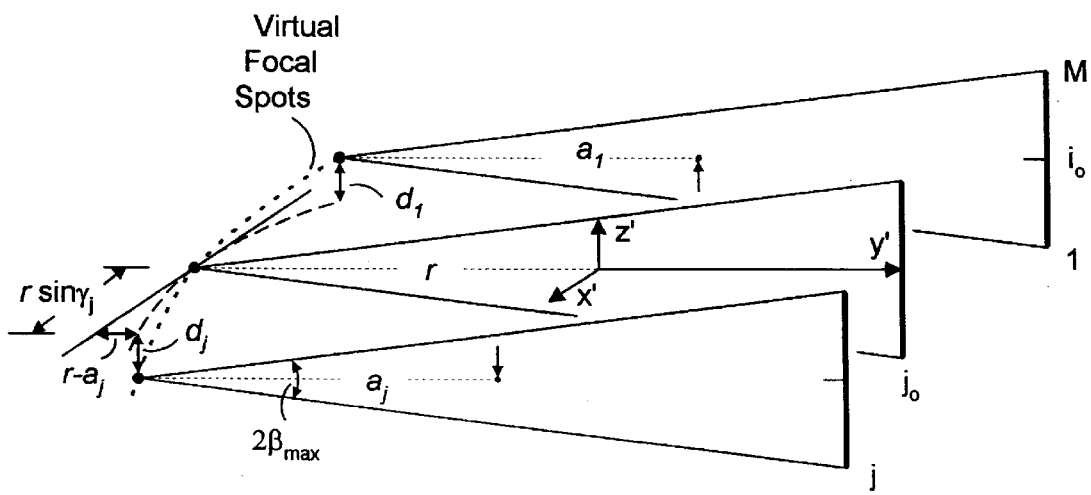
FIG. 7 is a schematic diagram of reordered rays from a helical scan illustrating slight distortion from wedge shape due to translation along the longitudinal axis.

The reordered rays of a helical scan are slightly distorted from the wedge shape, as shown in FIG. 7 at the view angle of $\phi=0°$. Unlike a step-and-shoot scan, the virtual longitudinal fans are no longer at the same z position. This is because the data of each virtual longitudinal fan are actually collected at a different time. The central longitudinal fan (of column $j_o$) is the only one collected at rotation angle of $\phi=0°$. The first virtual longitudinal fan (of column j=1) is collected at a time ahead of rotation angle $\theta=0°$, and it is offset from the central fan in the +z direction. Similarly, the last virtual longitudinal fan (of column j=N) is collected at a time after the rotation angle $\theta=0°$, and therefore it is offset from the central fan in the −z direction. If the pitch of the helical scan is 2p, the offset for the virtual longitudinal fan j in z direction is given by $$d_j = -p\gamma_j/\pi = -p(j-j_o)\delta/\pi \qquad (3)$$

A slice is selected as the common plane for convolution, and the projection data are interpolated to that plane. However, because of the cone angle, no slice is coplanar with the rays in all view angles. That is, more than one ray of the longitudinal fan intersects the slice. The ray passing the middle point of the slice can be considered as nearest to the slice, and it will be the ray to be interpolated from that longitudinal fan.

Figure 8:
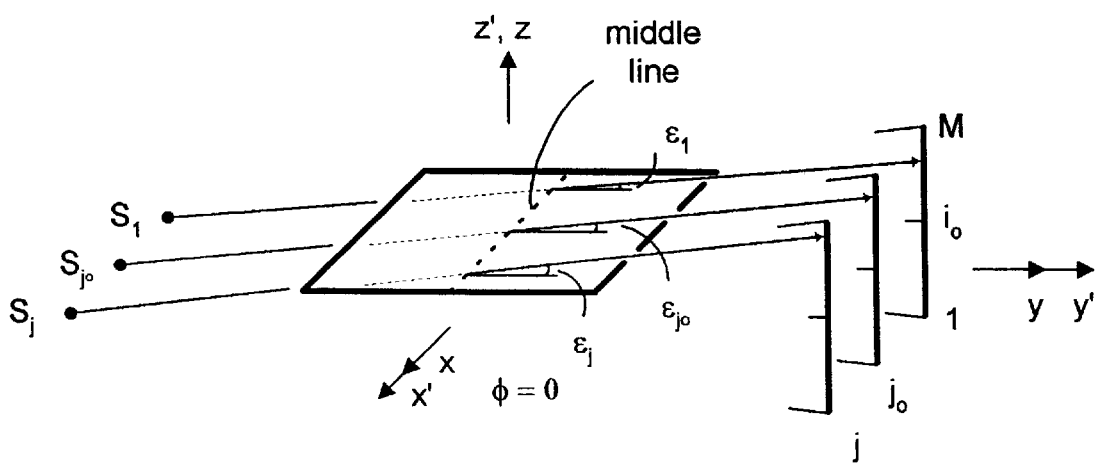
FIG. 8 is a schematic diagram illustrating aberration angles in a normal slice.

There are N middle points on the slice, one for each longitudinal fan. These middle points define a middle line, which is a line on the slice passing through the z-axis and perpendicular to the longitudinal fans. Its orientation varies with the view angle. Suppose a normal slice is selected for convolution. The middle line is the line y=0 at view angle of $\phi=0°$, as shown in FIG. 8. The angle between the slice and the ray intersecting the middle line is referred to as the aberration angle. It varies with the channel and the view angle. The aberration angle of channel j is illustrated in FIG. 8 as $\epsilon_j$.

Figure 9A:
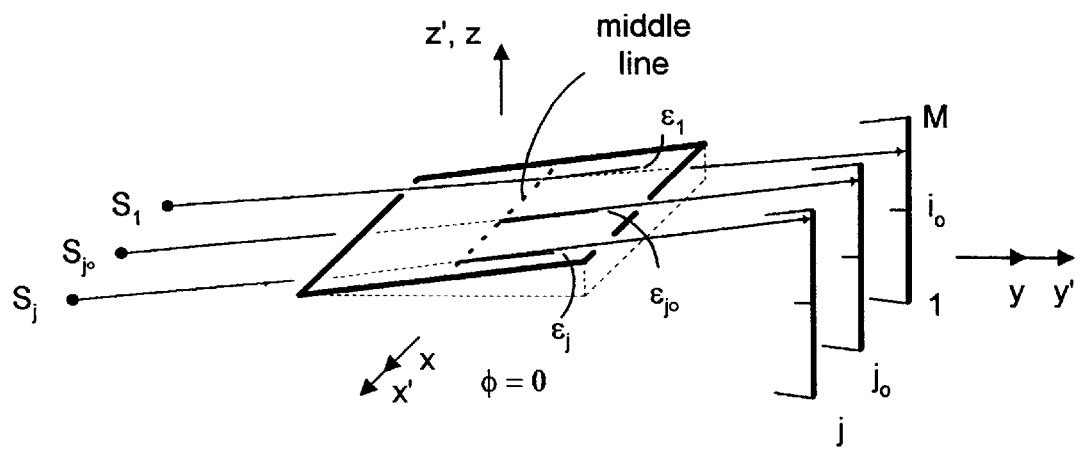
FIGS. 9A and 9B are schematic diagrams illustrating aberration angles in an oblique slice at view angles of 0 and 90 degrees, respectively.
Figure 9B:
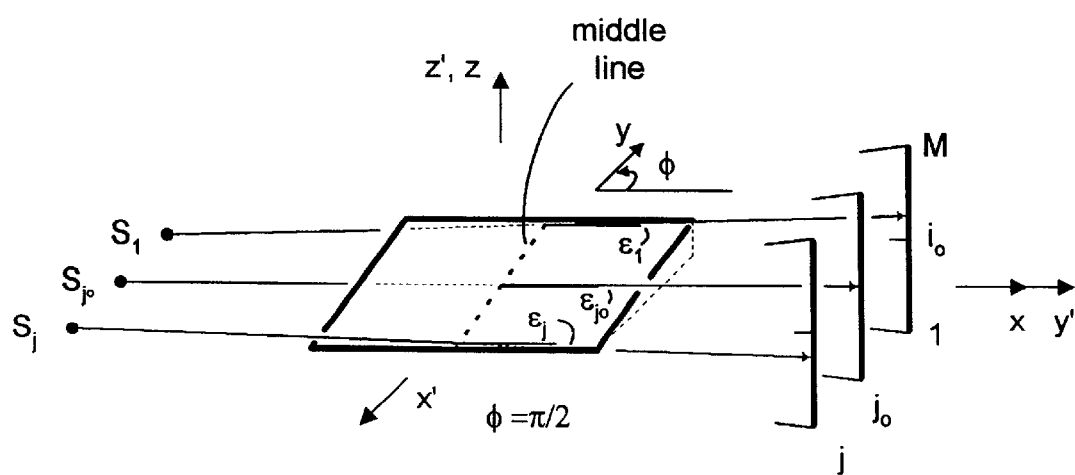

The magnitude of the aberration angles from all channels indicates the closeness of the slice being coplanar with the rays. The optimal slice for reconstruction is the one with the smallest aberration angles. An oblique slice can have smaller aberration angles than the normal slice. The aberration angle $\epsilon_j$ of an oblique slice is shown in FIG. 9A at view angle of $\phi=0°$, and in FIG. 9B at a view angle of $\phi=90°$. As shown in FIG. 9A, the aberration angles of an oblique slice at a view angle of $\phi=0°$ are less than those of a normal slice. As shown in FIG. 9B, the aberration angles of the oblique slice at a view angle of 90° are also smaller than those of the normal slice.

For ease of understanding of the description, processing of only one oblique slice for interpolation of projection profiles will be described. It will be understood that the description can be extended to any number of slices. Let (u,v) be a rectilinear coordinate on the slice with the u-axis being the line intersected by the xy-plane. The oblique slice can be considered to be the result of rotating a normal slice about the u-axis for an angle $\alpha$. The angle $\alpha$ is the oblique angle of the slice.

Figure 10A:
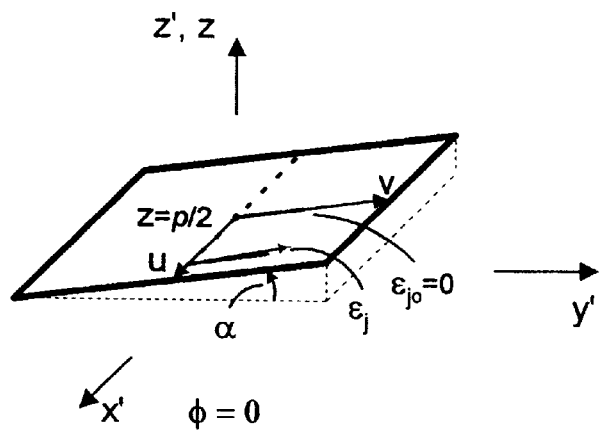
FIGS. 10A, 10B and 10C are schematic diagrams illustrating an oblique slice in accordance with the invention at view angles of 0, 90 and 180 degrees, respectively.

An oblique slice in accordance with the invention at view angle of $\phi=0°$ is depicted in FIG. 10A, where the oblique angle $\alpha$ is the angle between the v-axis and y'-axis. In one embodiment, it is preferred to select the oblique angle $\alpha$ such that the v-axis is coincident with a ray of the central longitudinal fan. In that case, the aberration angle of the central channel is zero, i.e., $\epsilon_{jo}=0$. The oblique slice is selected at a center location of p/2 with a slope of tan$\alpha$ in the +y' direction. Because the z position of any other longitudinal fan is offset from the central longitudinal fan by $d_j$ given in Equation (3) in the reordered parallel-beam geometry, the aberration angle of other channels are non-zero. Nevertheless, they are small and get smaller as the channel is closer to the central channel. The aberration angle $\epsilon_j$ of a channel j far away from the central channel is depicted in FIG. 10A.

Figure 10B:
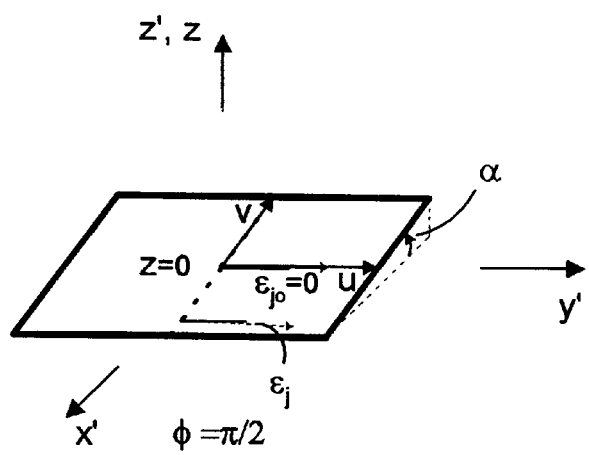

At a pitch of 2p for the helical scan, the oblique slice is preferably selected at a location along the z axis with its center at z=p/2. Then, at a view angle of $\phi=\pi/2$, the center of the slice will have traveled by p/2 to the location of the isocenter as shown in FIG. 10B. The oblique slice is traveled to z=0 with the slope tan $\alpha$ in the −x' direction. The u-axis becomes coincident with the central ray of the central longitudinal fan. Again, the aberration angle of the central channel is zero, $\epsilon_{jo}=0$, while other channels $\epsilon_j \neq 0$.

Figure 10C:
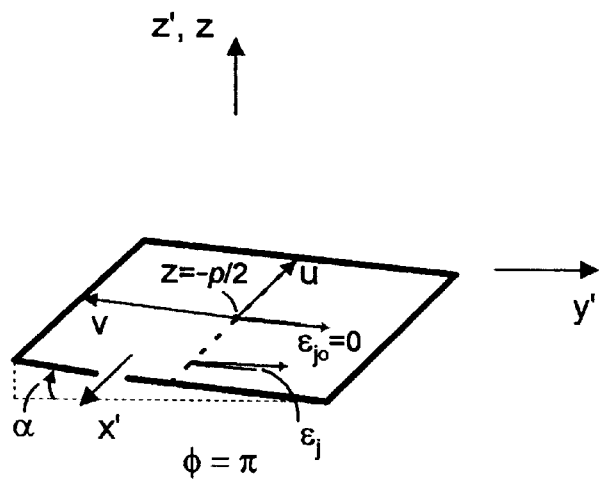

At a view angle of $\phi=\pi$, the geometry of the oblique slice is as shown in FIG. 10C. Here, the v-axis becomes coincident with another ray of the central longitudinal fan and $\epsilon_{jo}=0$. The oblique slice has traveled a distance p. The oblique slice is further traveled to z=−p/2 with the slope tan$\alpha$ in the −y' direction. For reconstructing the image from a half scan, the data at view angle $\phi=\pi$ is redundant with that at view angle $\phi=0$. The figure is shown here for better demonstration of the oblique slice, in general the projection data of the oblique slice at $\phi=\pi$ are not needed.

It should be noted that when an oblique slice is coincident with a ray of the central longitudinal fan the focal spot is lying on the slice plane. In that case, the oblique slice will be coplanar with a transverse fan containing this ray. Therefore the oblique slice shown in FIG. 10 is coplanar with a transverse fan of the divergent cone-beam data at rotation angles of $\phi=0, \pi/2$, and $\pi$.

It is not necessary to choose the oblique slice with exactly a null aberration angle at the central channel at $\phi=0, \phi=\pi/2$, and φ=π. Any oblique slice close to the oblique angle described here is acceptable. As can be seen from the figures, the oblique angle α is roughly equal to one half the cone angle, that is, α=β$_{max}$. In fact, α is preferably less than β$_{max}$, because the pitch 2p is usually shorter than the z dimension of the detector array at the isocenter.

Figure 11:
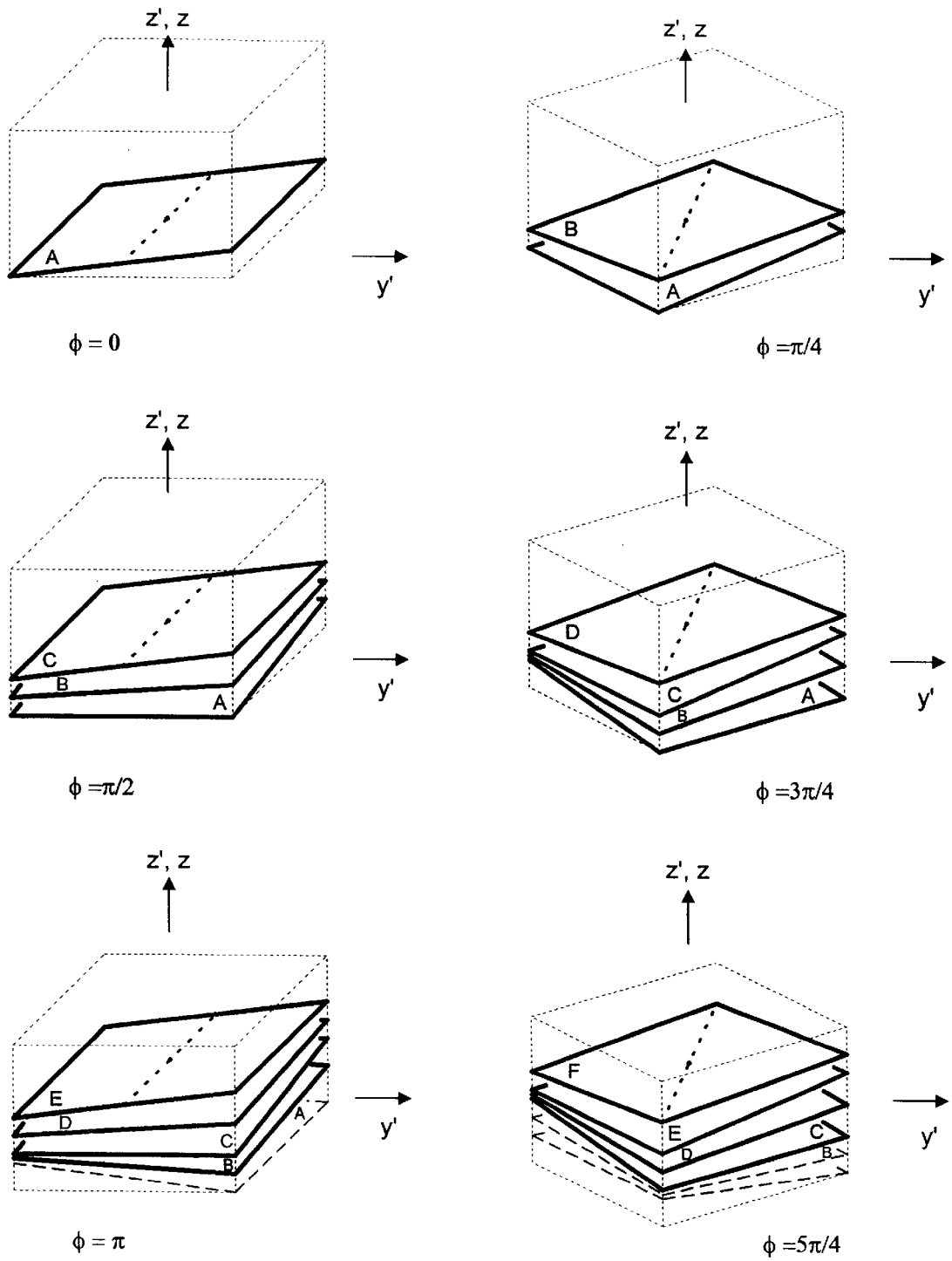
FIG. 11 schematically illustrates formation of a stack of oblique slices at multiple view angles in accordance with the invention.

In practice, the projection data are interpolated to multiple oblique slices at successive locations in the z direction for convolution. As an example, assume four slices are selected as references for the interpolation over the length of p in the z dimension, where p is the translation distance of the object during 180° rotation of the rotating frame. At a view angle φ=0, the first slice A is selected as illustrated in FIG. 10A and reproduced in FIG. 11. At view angle φ=π/4, the second slice B is selected as if it were at zero view angle as in FIG. 10A. In the meantime, the first slice has traveled for p/4 and oriented at an azimuth angle of 45° with respect to the rotating frame x'y'z, as shown in FIG. 11 for φ=π/4. Similarly, the third slice C and fourth slice D are selected at view angle of φ=π/2 and φ=3π/4, respectively, as if they were at zero view angle. At view angle φ=π, the fifth slice E is selected, while the interpolation for the projection profiles of first slice A has been completed.

From there on, at every π/4 interval one new slice is selected and one slice has completed the π view angle range as shown in the instance φ=5π/4 of FIG. 11. Thus, there are four slices for the interpolation of projection profile at each view angle starting from φ=3π/4. These four slices are located over the length p in z dimension.

In general, if m oblique slices are required for the interpolation at each view angle, the interval of view angle to select a new slice is π/m. Let Φ$_k$ be the view angle where the k slice is first selected as if it were at zero view angle, we have $$\Phi_k = k\pi/m \quad (4)$$

with k=0, 1, 2, . . . , m$_k$−1, and m$_k$ is the total number of slices to be selected over the whole length of the object. At the view angle of φ=π−π/m and thereafter, there will be m slices within the length p at each view angle. Given a view angle φ, these m slices are the slices with Φ$_k$ in the range of φ−π<Φ$_k$≦φ. They all have the same oblique angle α. However they are separated by a constant distance of p/m along z-axis, and oriented at different azimuth angles of π/m apart.

The selected oblique slices are not exactly coplanar with the rays. With the exception of a few rays in a few view angles, no ray is exactly coincident with the oblique slice. For each channel, the ray intersecting the center location of the slice is considered as the one nearest to the slice, and it is the ray to be interpolated from the original rays measured by the detector array. The intersecting points of these nearest rays for the N channels are lying in a line on the slice, which is referred to as the middle line. In order to interpolate the nearest ray from the original rays for each channel, the location of the middle line in the rotating frame must be known at each view angle.

In the reordered parallel-beam geometry, the projection data P$_{ij}$(φ) can be considered as consisting of N longitudinal fans, as shown in FIG. 7. The rays of longitudinal fan j are lying on an y'z'-plane parallel to that of the central longitudinal fan j$_o$, but separated by a distance of r sin((j−j$_o$) δ) in the x' direction. The longitudinal fan j is also offset from the central longitudinal fan J$_o$ by d$_j$, in z' direction and by r−a$_j$ in the y' direction, as described above. The middle line of the oblique slice k is perpendicular to the longitudinal fan j. It is lying on the x'z'-plane with y'=0. Given the oblique angle α and the view angle φ, the slope of the middle line on the x'z'-plane can be determined. Based on the slope, the z position of the middle line at channel j can be derived from the z position of the middle line at the central channel j$_o$.

Firstly, since the oblique slices are separated by p/m and translating along z-axis at the rate of distance p over view angle of π, the z position of the middle line at the central channel can be written as $$z_{kjo} = z_o + kp/m - \phi p/\pi \quad (5)$$

where z$_o$ is a constant representing the z position of the first slice at starting view angle of φ=0, and k is the slice number with k=0, 1, 2, . . . , m$_k$−1. Secondly, in order to find the slope of the middle line, we start with the simple geometry of the oblique slice when it was selected at φ=Φ$_k$. As can be seen from FIG. 10A and the φ=0 diagram of FIG. 11, the slope of the oblique slice is tan α along the y' direction. Thus, the z' coordinate of the oblique slice at φ=Φ$_k$ can be written as $$z'(\Phi_k) = z_{kjo} + y' \tan \alpha. \quad (6)$$

The middle line is the line of y'=0 on the slice. We see that the middle line at φ=Φ$_k$ has constant coordinate of z'=z$_{kjo}$, and the middle line is parallel to the x' axis as shown in FIG. 10A.

At a subsequent view angle of φ>Φ$_k$, the middle line can be located by rotating the oblique slice about the z'-axis for an angle of φ−Φ$_k$ and set the y' coordinate to 0. When the oblique slice is rotated about the z'-axis for φ−Φ$_k$, the z' coordinate of the oblique slice becomes $$z'(\phi) = z_{kjo} - x' \tan \alpha \sin(\phi - \Phi_k) + y' \tan \alpha \cos(\phi - \Phi_k). \quad (7)$$

The middle line is given by Equation (7) with y'=0. In addition, we know that the x' coordinate of the middle line is r sin((j−j$_o$)δ) for channel j. Thus, by further setting x'=r sin((j−j$_o$)δ) to Equation (7), we have the z position of the middle line at channel j as $$z_{kj}(\phi) = z_{kjo} - r \tan \alpha \sin(\phi - \Phi_k) \sin(j - j_o)\delta) \quad (8)$$

for the oblique slice k at a view angle of φ>Φ$_k$. Using Equation (5) for z$_{kjo}$, it becomes $$z_{kj}(\phi) = z_o + kp/m - \phi p/\pi - r \tan \alpha \sin(\phi - \Phi_k)\sin(j - j_o)\delta). \quad (9)$$

This point of the middle line is intersected by the ray to be interpolated. Thus, z$_{kj}$(φ) is also considered as the z position of the interpolated ray. In general, the z position of a ray interpolated from a longitudinal fan on y'z'-plane is defined by the z coordinate of the ray at y'=0.

Figure 12:
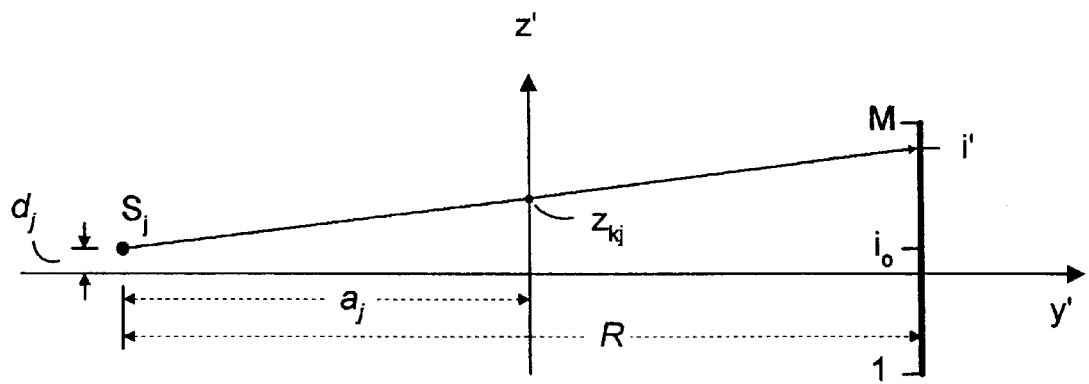
FIG. 12 schematically illustrates a ray to be interpolated from a longitudinal fan in accordance with the invention.

To interpolate a ray from the longitudinal fan, we notice that the oblique slice k is measured by the detector array for view angles between φ=Φ$_k$ and φ=Φ$_k$+π. Within that angular range, the corresponding detector row number of the ray intersecting the middle line is related to the z position z$_{kj}$(φ) by $$i' = i_o + (z_{kj} - d_j)R/a_j \quad (10)$$

assuming z$_{kj}$ and d$_j$ are measured in terms of the number of rows of detectors. The geometry of the ray with respect to the longitudinal fan j is shown in FIG. 12, where i$_o$ is the central row number and R is distance from the focal spot S$_j$ to the column of M detectors. The value i' in Equation (10) is not an integer number. It can be written as the sum of a truncated integer q and a fractional part f $$i' = q + f \quad (11)$$

with $0 \leq f < 1$. If a linear interpolation method is used to interpolate for the projections of the oblique slice, the interpolated projection value $P_{i'j}(\phi)$ for channel j will be calculated as $$P_{i'j}(\phi) = (1-f) P_{qj}(\phi) + f P_{q+1,j}(\phi) \quad (12)$$

Although linear interpolation provides a method of obtaining the projection value $P_{i'j}(\phi)$, it is not the only possible choice for the interpolation. For example, if the slice width is greater than the height of one detector (length along z-axis), the data can be over-sampled in the z dimension. A resampling method, such as the approach described in a copending U.S. Patent Application entitled, "An Improved Cone-Beam CT System With Over Sampling Detector Array and Resampling Technique," by C. M. Lai, filed on even date herewith, assigned to the same assignee as the present application U.S. Ser. No. 09/375,151, incorporated herein by reference, can be used to calculate for the projection value $P_{i'j}(\phi)$.

There are N projection values $P_{i'j}(\phi)$ to be calculated at each view angle. The rays of these interpolated projections are approximately coplanar with the oblique slice. Thus, it is a good approximation to convolute the interpolated projections in the same way as the projection data of the oblique slice. However, they will be backprojected along the paths of the interpolated rays, rather than the projection paths of the oblique slice. It is convenient to denote $P_{i'j}(\phi)$ as $P_{kj}(\phi)$, to indicate that $P_{i'j}(\phi)$ are processed for convolution like the projection data of the oblique slice k. That is, $$P_{kj}(\phi) = P_{i'j}(\phi) \quad (13)$$

with $k=0, 1, \ldots, m_k-1$, and $j=1, 2, \ldots, N$. At view angle $\phi$, there are m oblique slices, each with $\Phi_k$ in the range of $\phi - \pi < \Phi_k \leq \phi$, measured by the detector array. Thus, there are mN projection values $P_{kj}(\phi)$ to be interpolated for m slices in N channels at each view angle.

At each view angle, m projection profiles are interpolated according to m reference slices. Each projection profile contains N projection values $P_{kj}(\phi)$, with $j=1, 2, \ldots, N$ for oblique slice k. The rays of these N projection values are separated by a variable spacing in the lateral dimension (the x' dimension). This is because the longitudinal fan j is at a nonlinear distance of $r \sin \gamma_j = r \sin(j-j_o) \delta$ from the central longitudinal fan $j_o$, as shown in FIGS. 5 and 7.

For the subsequent convolution operation, it is required that these projection values are sampled at a constant lateral spacing. Therefore, the projection data $P_{kj}(\phi)$ are interpolated into equal lateral spacing at every view angle, like the parallel-beam projection data of a conventional single-row detector system. The lateral spacing at the central channel is $r \sin \delta = r \delta$. If $r \delta$ is chosen as the constant spatial interval for all channels, the projection data $P_{kj}(4)$ will be interpolated into a constant spacing of $r \delta$. The interpolation is performed among the N channels of each slices, independent of other slices.

This equal lateral spacing interpolation can also be performed on the original data $P_{ij}(\phi)$ collected by each row of detectors, before they are used to calculate the projection values of the oblique slices. In that case, the parallel projections $P_{ij}(\phi)$ reordered from each row are interpolated into equal lateral spacing of say $r \delta$. With the N channel in equal spacing, the z position of the channel j in Equation (9) becomes $$z_{kj}(\phi) = z_o + kp/m - \phi p/\pi - r \tan \alpha \sin(\phi - \Phi_k)(j - j_o)\delta. \quad (14)$$

Based on the equal spaced $P_{ij}(\phi)$ and Equation (14), the projection data $P_{kj}(\phi)$ interpolated to the oblique slice k will have equal lateral spacing of $r \delta$.

The N projection values of $P_{kj}(\phi)$ at equal spacing are then convoluted with a well-known convolution kernel for reconstruction of a 2D image. The convolution is performed at each view angle for each slice, in the same manner as in a conventional system with a single row of detectors. Let the convoluted projection value be $Q_{kj}(\phi)$. The convoluted projections $Q_{kj}(\phi)$ have equal spacing of $r \delta$ between adjacent channels. Whether this equal lateral spacing is performed before or after the generation of oblique-slice projections $P_{kj}(\phi)$, the z position of the convoluted projection $Q_{kj}(\phi)$ is given by $z_{kj}(\phi)$ in Equation (14), where the N channels are at a constant lateral spacing of $r \delta$.

The convoluted projection data $Q_{kj}(\phi)$ are used for 3D backprojection. The computation is usually voxel driven, in which all voxels in the 3D matrix are processed in sequential order at each view angle. At each voxel, the ray which passes through the voxel is determined and the corresponding convoluted projection value of this ray is interpolated from the nearest $Q_{kj}(\phi)$ values and added to the voxel.

The ray of each $Q_{kj}(\phi)$ is a line between the focal spot and a point on the middle line of the oblique slice. The rays of $Q_{kj}(\phi)$ for different slices of the same channel j are derived from the same longitudinal fan. Since the oblique slices are not parallel to each other, the rays of $Q_{kj}(\phi)$ are not equally spaced on the longitudinal fan. The only exception is the rays $Q_{kjo}(\phi)$ in the central channels. The spacing of the rays can be seen from the non-equally spaced middle points marked as dots along z' direction in FIG. 13.

The non-equal spacing of these rays on a longitudinal plane make the backprojection of $Q_{kj}(\phi)$ time consuming. All the voxels lying on the same plane as the longitudinal fan will have to interpolate $Q_{kj}(\phi)$ in non-equal spaced rays. The amount of computation required is considerably greater than the case of interpolating $Q_{kj}(\phi)$ in equal spaced rays. A technique is described here to pre-interpolate $Q_{kj}(\phi)$ in the same longitudinal fan into data of equally spaced rays. The computations for the 3D backprojection are largely simplified by using these equally spaced data.

Figure 13:
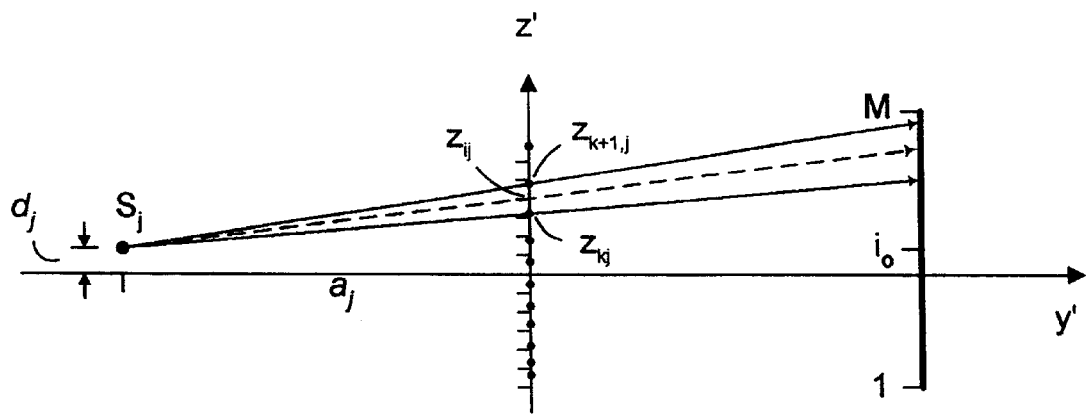
FIG. 13 is a schematic diagram illustrating unequal spacing between rays intersecting oblique slices.

In accordance with this aspect of the invention, the z-positions of the central channel, $z_{kjo}$, are given in Equation (5) with a constant interval of $p/m$ between adjacent slices as marked in equally spaced divisions along the z'-axis of FIG. 13. It is preferred to pre-interpolate $Q_{kj}(\phi)$ of other channels into the same spacing as the central channel. The m rows of data $Q_{kj}(\phi)$ are then pre-interpolated into m rows of $R_{ij}(\phi)$ at equally spaced z positions, with $z_{ij} = z_{ijo}$ at each view angle. It should be noted that the z position of a ray is referred to as the z coordinate of the ray at the location of $y'=0$.

To interpolate for ray i of channel j, the two z-positions of $Q_{kj}(\phi)$ adjacent to the z-position of $R_{ij}(\phi)$, i.e., $z_{ij}$, must be found, with the relation $$z_{kj} \leq z_{ij} < z_{k+1j} \quad (15)$$

Using $z_{ij} = z_{ijo}$ and Equations (5) and (14), the above relation can also be written as $$k - r \tan \alpha \sin(\phi - \Phi_k)\sin \delta m/p \leq i < k - r \tan \alpha \sin(\phi - \Phi_{k+1}) \sin \delta m/p, \quad (16)$$

from which the number k is determined and the two values $Q_{kj}(\phi)$ and $Q_{k+1,j}(\phi)$ are used to interpolate for $R_{ij}(\phi)$.

If a linear interpolation method is used, we have $$R_{ij}(\phi) = (1-g) Q_{kj}(\phi) + g Q_{k+1,j}(\phi) \quad (17)$$

where $$g = (z_{ij} - z_{kj})/(z_{k+1,j} - z_{kj}) \quad (18)$$

The above equations describe a simple way of interpolating $R_{ij}(\phi)$ from $Q_{kj}(\phi)$. Alternatively, a higher-order interpolation method can be used to generate equally spaced $R_{ij}(\phi)$ from $Q_{kj}(\phi)$.

When the equally spaced $R_{ij}(\phi)$ are used for 3D backprojection, the value to be backprojected to a voxel still needs to be interpolated from $R_{ij}(\phi)$. Because of repetition of this operation, linear interpolation is usually used to save the computing time. Under linear interpolation, the value is assumed to vary linearly between two adjacent points of $R_{ij}(\phi)$. However, they are not necessarily linear, particularly when these two values, $R_{ij}(\phi)$ and $R_{i+1,j}(\phi)$, are interpolated from different adjacent values of $Q_{kj}(\phi)$. The accuracy of the backprojecting values can be improved by pre-interpolating more numbers of rows of $R_{ij}(\phi)$ from $Q_{kj}(\phi)$.

For example, if m rows of $Q_{kj}(\phi)$ are pre-interpolated into 4m rows of $R_{ij}(\phi)$, the z-positions of $R_{ij}(\phi)$ are at constant interval of p/4m with $$z_{ij}=z_{ijo}=z_o+i\,p/4m-\phi p/\pi \quad (19)$$

Using Equation (15), we have the relation $$4k-r\tan\alpha\sin(\phi-\Phi_k)\sin\delta 4m/p \le i < 4k-r\tan\alpha\sin(\phi-\Phi_{k+1})\sin\delta 4m/p \quad (20)$$

to find the row number k of $Q_{kj}(\phi)$. Then, from the row number k, $R_{ij}(\phi)$ can be generated by linear interpolation as given in Equations (17) and (18), or by higher order interpolation. In prior methods, the collected projection data were interpolated into normal slices for convolution, as described in, for example, pending U.S. patent application Ser. No. 09/038,320, entitled, "Method and Apparatus for Reconstructing Volumetric Images in a Helical Scanning Computed Tomography System with Multiple Rows of Detectors," by C. M. Lai, filed on Mar. 11, 1998, of common assignee, the contents of which are incorporated herein in their entirety by reference. In the present method, the collected projection data are interpolated into oblique slices for convolution, and the convoluted data are further pre-interpolated into $R_{ij}(\phi)$ with equally spaced z positions. The geometry of the rays in $R_{ij}(\phi)$ is similar to the geometry of the rays in the convoluted data of prior methods. Therefore, in one embodiment, prior techniques of backprojection can be used to backproject the data $R_{ij}(\phi)$ onto a 3D image matrix.

In the 3D backprojection of the invention, the coordinate of a voxel in the rotating frame (x',y',z') is first calculated from its location in the laboratory frame (x,y,z) as $$x'=x\cos\phi-y\sin\phi$$
$$y'=x\sin\phi+y\cos\phi$$
$$z'=z \quad (21)$$

It is assumed that the 3D matrix includes $m_q$ normal slices with slice width of t. If the voxel is in slice q, with q=0, 1, 2, ..., $m_q-1$. The location of the voxel in the z dimension with respect to the first normal slice is q t. Using Equation (1) for the first normal slice with $\theta=\phi$, the z' coordinate of the voxel becomes $$z'=qt+z_o-p\phi/\pi \quad (22)$$

The channel number j of the ray passing the voxel can be determined from the x' coordinate. Firstly, the z position of this ray is calculated by $$z_v=z'(a_j-y')/a_j=(qt+z_o-p\phi/\pi)(a_j-y')/a_j \quad (23)$$

Based on the z position $z_v$, the convoluted projection value to be backprojected to the voxel is interpolated from two adjacent rays, $R_{ij}(\phi)$ and $R_{i+1,j}(\phi)$, with z positions nearest to $z_v$, i.e., $$z_{ij} \le z_v < z_{i+1,j} \quad (24)$$

Since the z positions $z_{ij}$ are in equal intervals, the row number i can be calculated as a truncated integer of $z_v$.

Although it is preferred to pre-interpolate the convoluted projection data $Q_{kj}(\phi)$ of multiple oblique slices into $R_{ij}(\phi)$, it is also possible to backproject the data $Q_{kj}(\phi)$ directly into the 3D image matrix. In that case, the two adjacent rays, $Q_{kj}(\phi)$ and $Q_{k+1,j}(\phi)$, to be used for interpolating the ray passing the voxel, are determined by $$z_{kj} \le z_v < z_{k+1,j} \quad (25)$$

The interpolation is carried out the same manner as given in Equations (16), (17) and (18). However, the z positions $z_{kj}$ do not have a constant interval here, and thus the interpolation will take a considerable number of computations.

In accordance with one aspect of the invention, a more accurate method is developed to reconstruct volumetric image data from cone-beam projection data. A set of oblique slices is selected within the reconstruction volume, and the projection data are interpolated to the rays most coplanar with these oblique slices. Each slice is selected at such an angle that the focal spot is nearest to the plane of the slice at all view angles. These oblique slices have the same oblique angle, but they are not parallel to each other because of different azimuth angles. The convolution based on these interpolated projection data is more accurate for reconstruction of the volumetric image than prior methods, where the convolution is based on projection data interpolated nearest to a set of normal slices.

Like the rays of the collected data, these interpolated rays are divergent from the focal spot. Accurate 3D backprojection can be performed, since the geometry of these interpolated rays is precisely known. However, these interpolated rays are not equally spaced in the z dimension. To speed up the backprojection, a technique is applied to pre-interpolate the convoluted data into equal spacing in the z dimension.

The computing time of reconstructing a volumetric image is dominated by the 3D backprojection. Although the interpolation or resampling of the projection data to oblique slices and the pre-interpolation of the convoluted data are not straightforward, the computing time is insignificant compared to the 3D backprojection. Furthermore, lookup tables can be used to store the interpolation addresses and coefficients, which can reduce the computing time of these two operations.

The detectors of the detector array are assumed here to have equal height, that is equal length along the z-axis, for all rows of detectors. In practice, the detectors of the detector array can have different heights among different rows of detectors as described in U.S. patent application Ser. No. 09/159,067, entitled, "CT Scanner Comprising a Spatially Encoded Detector Array Arrangement and Method," by Bernard M. Gordon, filed on Sep. 23, 1998 U.S. Ser. No. 09/159,067, incorporated herein by reference. In that case, one possibility is to first combine or resample the collected data into multiple rows of projection data in equal height as described in pending U.S. Patent Application entitled, "An Improved Cone-Beam CT System With Oversampling Detector Array and Resampling Technique," by C. M. Lai, filed on even data herewith, U.S. Ser. No. 09/375,151. The other possibility is to interpolate or resample the collected projection data directly to the selected oblique slices, in which the projection data are interpolated or resampled from a non-equal spacing into another non-equal spacing in the z dimension.

In the invention described herein, the projection data collected from each row of detectors are first reordered into parallel-beam projections as described above. It is also possible to interpolate the collected projection data to the oblique slices before the reordering process, like the practice used in U.S. Pat. No. 5,802,134, entitled, "Nutating Slice CT Image Reconstruction Apparatus and Method," by G. L. Larson, C. C. Ruth, C. R. Crawford. However, the mathematical equations for interpolation of the projection data and pre-interpolation of convoluted data will be more complicated.

While this invention has been particularly shown and described with references to preferred embodiments thereof, it will be understood by those skilled in the art that various changes in form and details may be made therein without departing from the spirit and scope of the invention as defined by the following claims.

For example, while the embodiments have been described with reference to third generation CT machines, the principles can be applied to other types of CT scanners such as fourth generation machines.

What is claimed is:

1. A method of reconstructing image data for a region having a longitudinal axis, comprising:

providing a radiation source and an array of detectors on opposed sides of the region, the radiation source emitting radiation toward the array of detectors to generate a plurality of diverging radiation beams received by the array of detectors, at least one of the radiation source and the array of detectors being rotatable about the longitudinal axis through a plurality of projection angles to scan the region to generate diverging beam scan data for the region;

converting the diverging beam scan data for the region into parallel beam scan data for the region;

defining at least one oblique slice for the region, said oblique slice being oblique with respect to the longitudinal axis;

using at least a portion of the parallel beam scan data for the region, generating projection data associated with the at least one oblique slice;

applying convolution to the projection data associated with the at least one oblique slice to generate convoluted projection data for the region; and applying three-dimensional back projection to the convoluted projection data associated with the at least one oblique slice to generate the image data for the region.

2. The method of claim 1 further comprising generating convoluted projection data associated with rays having equal spacing in the longitudinal direction for three-dimensional back projection.

3. The method of claim 1 wherein the array of detectors is a two-dimensional array of detectors.

4. The method of claim 1 wherein the plurality of diverging radiation beams form a cone beam of radiation.

5. The method of claim 1 wherein the diverging beam scan data is obtained by helical cone beam scanning of the region.

6. The method of claim 1 wherein an angle formed by the oblique slice and the longitudinal axis is selected such that the oblique slice is coplanar with the radiation source for at least one projection angle.

7. The method of claim 1 wherein an angle formed by the oblique slice and the longitudinal axis is selected such that the oblique slice is coplanar with the radiation source for three projection angles.

8. The method of claim 7 wherein for the at least one oblique slice, the three projection angles for which the oblique slice is coplanar with the radiation source are 0 degrees, 90 degrees and 180 degrees.

9. The method of claim 1 wherein the projection data associated with the at least one oblique slice is generated using parallel beam scan data for a ray intersecting the at least one oblique slice.

10. The method of claim 9 wherein the ray intersects the middle of the at least one oblique slice.

11. The method of claim 1 wherein the projection data associated with the at least one oblique slice is generated using diverging beam scan data for a ray intersecting the at least one oblique slice.

12. The method of claim 11 wherein the ray intersects the middle of the at least one oblique slice.

13. An apparatus for reconstructing image data for a region having a longitudinal axis, comprising:

a radiation source and an array of detectors on opposed sides of the region, the radiation source emitting radiation toward the array of detectors to generate a plurality of diverging radiation beams received by the array of detectors, at least one of the radiation source and the array of detectors being rotatable about the longitudinal axis to scan the region to generate diverging beam scan data for the region; and a processor for (i) converting the diverging beam scan data for the region into parallel beam scan data for the region, (ii) defining at least one oblique slice for the region, said oblique slice being oblique with respect to the longitudinal axis, (iii) using at least a portion of the parallel beam scan data for the region, generating projection data associated with the at least one oblique slice, (iv) applying convolution to the projection data associated with the at least one oblique slice to generate convoluted projection data for the region, and (v) applying three-dimensional back projection to the projection data associated with the at least one oblique slice to generate the image data for the region.

14. The apparatus of claim 13 wherein the processor generates convoluted projection data associated with rays having equal spacing in the longitudinal direction for three-dimensional back projection.

15. The apparatus of claim 13 wherein the array of detectors is a two-dimensional array of detectors.

16. The apparatus of claim 13 wherein the plurality of diverging radiation beams form a cone beam of radiation.

17. The apparatus of claim 13 wherein the diverging beam scan data is obtained by helical cone beam scanning of the region.

18. The apparatus of claim 13 wherein an angle formed by the oblique slice and the longitudinal axis is selected such that the oblique slice is coplanar with the radiation source for at least one projection angle.

19. The apparatus of claim 13 wherein an angle formed by the oblique slice and the longitudinal axis is selected such that the oblique slice is coplanar with the radiation source for three projection angles.

20. The apparatus of claim 19 wherein for the at least one oblique slice, the three projection angles for which the oblique slice is coplanar with the radiation source are 0 degrees, 90 degrees and 180 degrees.

21. The apparatus of claim 13 wherein the processor generates the projection data associated with the at least one oblique slice using parallel beam scan data for a ray intersecting the at least one oblique slice.

22. The apparatus of claim 21 wherein the ray intersects the middle of the at least one oblique slice.

23. The apparatus of claim 13 wherein the processor generates the projection data associated with the at least one oblique slice using diverging beam scan data for a ray intersecting the at least one oblique slice.

24. The apparatus of claim 23 wherein the ray intersects the middle of the at least one oblique slice.

25. A CT scanner comprising:

a source that generates a cone beam of radiation;

a plurality of detectors that are arranged and positioned relative to the source so that as the source rotates about a rotation axis the cone beam is projected onto the detectors as a plurality of diverging beams and projected data is collected from the detectors; and a processor constructed and arranged so as to (a) interpolate the projected data into slice data representative of oblique slices; (b) convolve the slice data into convolved data; (c) pre-interpolate the convolved data into reordered projection data with equally spaced axial positions relative to the rotation axis.

26. A CT scanner comprising:

a source that generates a cone beam of radiation;

a plurality of detectors that are arranged and positioned relative to the source so that as the source rotates about a rotation axis the cone beam is projected as rays through a scanned volume onto the detectors so as to generate cone beam projection data; and a processor constructed and arranged so as to interpolate the projection data to rays most planar with a preselected set of oblique slices through the scanned volume;

wherein the preselected set of oblique slices is selected such that each oblique slice has the same oblique angle.

27. A CT scanner according to claim 26, wherein the source rotates through a plurality of view angles during a scan, and the preselected set of oblique slices is selected such that the angle of each slice relative to the rotation axis results in the focal spot being nearest to the plane of the slice at all of said view angles.

* * * * *